(12) United States Patent
Matsuda et al.

(10) Patent No.: US 7,320,883 B2
(45) Date of Patent: Jan. 22, 2008

(54) PROCESS FOR PRODUCING COENZYME $Q_{10}$

(75) Inventors: Hideyuki Matsuda, Matsue (JP); Makoto Kawamukai, Matsue (JP); Kazuyoshi Yajima, Akashi (JP); Yasuhiro Ikenaka, Kobe (JP)

(73) Assignee: Kaneka Corporation, Osaka-shi (JP)

( * ) Notice: Subject to any disclaimer, the term of this patent is extended or adjusted under 35 U.S.C. 154(b) by 442 days.

(21) Appl. No.: 10/450,681

(22) PCT Filed: Dec. 27, 2001

(86) PCT No.: PCT/JP01/11523

§ 371 (c)(1),
(2), (4) Date: Jan. 23, 2004

(87) PCT Pub. No.: WO02/052017

PCT Pub. Date: Jul. 4, 2002

(65) Prior Publication Data

US 2004/0157286 A1    Aug. 12, 2004

(30) Foreign Application Priority Data

Dec. 27, 2000    (JP) ............................ 2000-398658

(51) Int. Cl.
*C12P 7/66*    (2006.01)
*C12N 15/54*   (2006.01)
*C12N 9/12*    (2006.01)

(52) U.S. Cl. .................. 435/133; 536/23.2; 435/320.1; 435/252.3; 435/252.33; 435/194

(58) Field of Classification Search ...................... None
See application file for complete search history.

(56) References Cited

U.S. PATENT DOCUMENTS 6,103,488 A    8/2000    Matsuda et al.

2004/0137567 A1 *  7/2004  Matsuda et al. ........... 435/69.1

FOREIGN PATENT DOCUMENTS

| CA | 2 348 161 | * | 3/2001 |
| EP | 0 812 914 A2 | | 12/1997 |
| EP | 1 123 979 A1 | | 8/2001 |
| EP | 1 336 657 A1 | | 8/2003 |
| JP | 56-92793 A | | 7/1981 |
| JP | 9-173076 A | | 7/1997 |
| JP | 10-57072 A | | 3/1998 |
| JP | 11-178590 A | | 7/1999 |
| WO | 01/14567 | * | 3/2001 |

OTHER PUBLICATIONS

J. Choi et al. "Biotechnological Production and Applications of Coenzyme Q10", Appl. Microbiol. Biotechnol. 68: 9-15 (2005).*

Koyama, T., et al., Thermostable Farnesyl Diphosphate Synthase of *Bacillus stearothermophilus*: Molecular Cloning, Sequence Determination, Overproduction, and Purification, *J. Biochem.*, vol. 113, No. 3, pp. 355-363 (1993).

Suh, S., et al., "Quantitative Differences of Nuclear DNA Contents and Their Taxonomic Implications in *Leucosporidium scottii*, *Rhodosporidium toruloides*, and Related Basidiomycetous Yeasts," *J. Gen. Appl. Microbiol.*, vol. 39, No. 3, pp. 295-302 (1993).

Suzuki, K., et al., "Analysis of the Decaprenyl Diphosphate Synthase (*dps*) Gene in Fission Yeast Suggests a Role of Ubiquinone as an Antioxidant," *J. Biochem*, vol. 121, No. 3, 1997, pp. 456-505.

* cited by examiner

Primary Examiner—Rebecca Prouty
(74) Attorney, Agent, or Firm—Kenyon & Kenyon LLP

(57) ABSTRACT

The invention aims at providing a process for producing coenzyme $Q_{10}$ efficiently in microorganisms by utilizing a coenzyme $Q_{10}$ side chain synthesis gene derived from a fungal species belonging to the genus *Aspergillus* and genus *Leucosporidium*.

The present invention relates to a DNA having a DNA sequence described under SEQ ID NO:1 and 2 or derived from the above sequence by deletion, addition, insertion and/or substitution of one or several bases and encoding a protein having decaprenyl diphosphate synthase activity.

11 Claims, 3 Drawing Sheets

CoQ₁₀ standard

E.coli JM109

E.coli JM109/pUCA1

PROCESS FOR PRODUCING COENZYME Q₁₀

This application is a 371 national phase application of PCT/JP01/11523 filed on 27 Dec. 2001, claiming priority to JP 2000-398658, filed on 27 Dec. 2000, the content of which is incorporated herein by reference in its entirety.

TECHNICAL FIELD

The present invention relates to a process for producing coenzyme $Q_{10}$, which is in use as a drug or the like. More particularly, it relates to a process for causing formation of coenzyme $Q_{10}$ by introducing a gene coding for a coenzyme $Q_{10}$ side chain synthase, which serves as a key enzyme in the biosynthesis of coenzyme $Q_{10}$, namely a decaprenyl diphosphate synthase into a microorganism.

BACKGROUND ART

An industrial process for producing coenzyme $Q_{10}$, which is conventional in the art, comprises, for example, isolating coenzymes of plant origin, for example of tobacco origin, and adjusting the side chain length thereof by a synthetic method.

It is known that coenzyme $Q_{10}$ is produced in a wide variety of organisms, from microorganisms, such as bacteria and yeasts, to higher animals and plants. Thus, the process comprising cultivating a microorganism and extracting this substance from cells thereof can be regarded as one of the most efficient process for producing coenzyme $Q_{10}$ and has actually been employed in commercial production thereof. However, the productivity of such processes can hardly be said to be good, since the yield is low and the procedure is complicated, for instance.

Attempts have also been made to increase the production of coenzyme $Q_{10}$ by isolating genes involved in the biosynthesis of coenzyme $Q_{10}$ and amplifying the genes utilizing the recombinant DNA technology. Coenzyme $Q_{10}$ is formed in vivo in a multistage process comprising complicated reactions in which a number of enzymes are involved. The route of biosynthesis thereof in prokaryotes partially differs from that in eukaryotes. Basically, however, each route comprises three fundamental steps, namely the step of synthesis of decaprenyl diphosphate, which is the source of the prenyl side chain of coenzyme $Q_{10}$, the step of synthesis of para-hydroxybenzoic acid, which is the source of the quinone ring, and the step of completion of coenzyme $Q_{10}$ through coupling of these two compounds and successive substituent conversions. Among these reactions, the reaction which determines the side chain length of coenzyme $Q_{10}$, namely the decaprenyl diphosphate synthase-involving reaction, which is said to be a rate-determining one in the whole biosynthetic reaction route, is considered to be the most important one.

Therefore, for efficient production of coenzyme $Q_{10}$, it is considered effective to isolate a decaprenyl diphosphate synthase gene, which is the key gene in the biosynthesis of coenzyme $Q_{10}$, and utilize the same for the purpose of increasing production. As for the gene source, fungi, in which coenzyme $Q_{10}$ is produced in relatively large amounts, are leading candidates.

So far, decaprenyl diphosphate synthase genes have been isolated from several microorganisms, such as *Schizosaccharomyces pombe* (JP-A-09-173076) and *Gluconobacter suboxydans* (JP-A-10-57072). However, the productivity of coenzyme $Q_{10}$ in these microorganisms cannot be said to be satisfactory, and the cultivation of these microorganisms and the separation/purification of coenzyme $Q_{10}$ therefrom have not been efficient. It has thus been desired that a microorganism-derived gene for that enzyme, which enables high level production of coenzyme $Q_{10}$, be isolated.

SUMMARY OF THE INVENTION

It is an object of the present invention to produce coenzyme $Q_{10}$ efficiently in microorganisms by isolating a coenzyme $Q_{10}$ side chain synthesis gene from a fungal species belonging to the genus *Leucosporidium* and genus *Aspergillus*, and utilizing the same to thereby solve the above-mentioned productivity problem.

For attaining the above object, in the present invention, firstly, investigations were made in an attempt to isolate a key gene involved in the biosynthesis of coenzyme $Q_{10}$, a decaprenyl diphosphate synthase gene from fungi belonging to the genus *Leucosporidium* and genus *Aspergillus* and succeeded in isolating such gene. This success has now led to completion of the present invention.

Thus, the present invention provides
a DNA of the following (a), (b) or (c):
(a) a DNA whose base or sequence is as described under SEQ ID NO:1;
(b) a DNA having a base sequence derived from the base sequence shown under SEQ ID NO:1 by deletion, addition, insertion and/or substitution of one or several bases and
encoding a protein having decaprenyl diphosphate synthase activity;
(c) a DNA capable of hybridizing with a DNA comprising the base sequence shown under SEQ ID NO:1 under stringent conditions and
encoding a protein having decaprenyl diphosphate synthase activity.

The invention further provides
a DNA of the following (d), (e) or (f):
(d) a DNA whose base sequence is as described under SEQ ID NO:2;
(e) a DNA having a DNA sequence derived from a base sequence shown under SEQ ID NO:2 by deletion, addition, insertion and/or substitution of one or several bases and
encoding a protein having decaprenyl diphosphate synthase activity;
(f) a DNA capable of hybridizing with a DNA comprising the base sequence shown under SEQ ID NO:2 under stringent conditions and
encoding a protein having decaprenyl diphosphate synthase activity.

The invention further provides
a protein of the following (g) or (h):
(g) a protein whose amino acid sequence is as described under SEQ ID NO:3;
(h) a protein having an amino acid sequence derived from the amino acid sequence shown under SEQ ID NO:3 by deletion, addition, insertion and/or substitution of one or several amino acid residues and having decaprenyl diphosphate synthase activity.

The invention further provides
a protein of the following (i) or (j):
(i) a protein whose amino acid sequence is as described under SEQ ID NO:4;
(j) a protein having an amino acid sequence derived from the amino acid sequence shown under SEQ ID NO:4 by deletion, addition, insertion and/or substitution of one or several amino acid residues and having decaprenyl diphosphate synthase activity.

The invention further provides

DNAs respectively encoding the above proteins (g) to (j).

The invention further provides expression vectors with the above DNAs inserted into vectors.

The invention further provides transformants resulting from transformation of host microorganisms with the respective DNAs mentioned above or with the expression vectors mentioned above.

The invention still further provides a process for producing coenzyme $Q_{10}$, which comprises cultivating any of the above-mentioned transformants in a medium and recovering coenzyme $Q_{10}$ thus formed and accumulated in the medium.

DETAILED DISCLOSURE OF THE INVENTION

The present inventors made investigations to isolate a gene encoding the enzyme in question from fungi belonging to the genus *Leucosporidium* and genus *Aspergillus*, in which coenzyme $Q_{10}$ is produced in relatively large amounts, and, as a result, succeeded in obtaining a fragment of the gene by the PCR method.

The sequence of a known gene encoding a decaprenyl diphosphate synthase was compared with that of a known gene encoding a polyprenyl diphosphate synthase which is an analogue of the enzyme in question and a long prenyl chain synthase of different chain length coenzyme Q, and various PCR primers were synthesized for regions showing high homology therebetween. PCR conditions were studied for various combinations of these primers and, as a result, it was revealed, by gene base sequence analysis, that when 40 PCR cycles, each comprising 94° C., 1 minute→43° C., 2 minutes→72° C., 2 minutes, are carried out after 3 minutes of heat treatment at 94° C., using the primers DPS-1 (SEQ ID NO:5 in the sequence listing) and DPS-1 1AS (SEQ ID NO:6 in the sequence listing), a fragment, about 220 bp in size, of the enzyme gene in question is amplified from the chromosomal gene of *Leucosporidium scotti* IFO 1212, which is a fungal species belonging to the genus *Leucosporidium* and *Aspergillus clavatus* JCM 1718, which is a fungal species belonging to the genus *Aspergillus*.

For obtaining the enzyme gene in its full length, mRNA is first prepared from a fungus body of *Leucosporidium scotti* IFO 1212 and *Aspergillus clavatus* JCM 1718 in order to respectively produce 5' terminal side sequence by 5'RACE method using a primer prepared based on the inner sequence obtained before and produce 3' terminal side sequence by conducting RT-PCR using oligo dT primer relative to a poly A sequence, which is specific for the mRNA.

The base sequence of the sequence obtained was determined, whereupon it was revealed that it has the sequence shown under SEQ ID NO:1 and NO:2 in the sequence listing. In the amino acid sequence predicted from this base sequence, there was found a sequence characteristic of decaprenyl diphosphate synthase.

The DNA of the present invention may be a DNA whose base sequence is as described under SEQ ID NO:1 or SEQ ID NO:2, or a DNA having a base sequence derived from the base sequence shown under SEQ ID NO:1 or SEQ ID NO:2 by deletion, addition, insertion and/or substitution of one or several bases and encoding a protein having decaprenyl diphosphate synthase activity, or a DNA capable of hybridizing with a DNA comprising the base sequence shown under SEQ ID NO:1 or SEQ ID NO:2 under stringent conditions and encoding a protein having decaprenyl diphosphate synthase activity. A number of amino acids each may be encoded by one or more codons (genetic code degeneracy), so that a number of DNAs other than the DNA having the base sequence shown under SEQ ID NO:1 or SEQ ID NO:2 can encode the protein having the amino acid sequence shown under SEQ ID NO:3 or SEQ ID NO:4. Therefore, the DNA of the invention includes such DNAs encoding the protein having the amino acid sequence shown under SEQ ID NO:3 or SEQ ID NO:4 as well.

The expression "base sequence derived by deletion, addition, insertion and/or substitution of one or several bases" as used herein means a base sequence resulting from deletion, addition, insertion and/or substitution of such a number of bases as can be deleted, added, inserted and/or substituted according to the methods well known to those skilled in the art, for example those described in Supplemental issue, Tanpakushitsu, Kakusan, Koso (Protein, Nucleic Acid and Enzyme), PCR Method for Gene Amplification, TAKKAJ, 35 (17), 2951-3178 (1990) or Henry A. Erlich (ed.), translated into Japanese under the supervision of Ikunoshin Kato: PCR Technology (1990).

The expression "DNA capable of hybridizing with a DNA comprising the base sequence shown under SEQ ID NO:1 (or SEQ ID NO:2) under stringent conditions" means a DNA obtainable by utilizing the technique of colony hybridization, plaque hybridization or southern hybridization, among others, using a DNA comprising the base sequence shown under SEQ ID NO:1 (or SEQ ID NO:2) as a probe. Those skilled in the art would be able to readily obtain the desired DNA by carrying out such hybridization according to the method described in Molecular Cloning, 2nd edition (Cold Spring Harbor Laboratry Press, 1989).

The expression "DNA capable of hybridizing with a DNA comprising the base sequence shown under SEQ ID NO: 1 (or SEQ ID NO:2) under stringent conditions" means a DNA obtainable by utilizing the technique of colony hybridization, plaque hybridization or southern hybridization, among others, using a DNA comprising the base sequence shown under SEQ ID NO: 1 (or SEQ ID NO:2) as a probe. Those skilled in the art would be able to readily obtain the desired DNA by carrying out such hybridization according to the method described in Molecular Cloning, $2^{nd}$ edition (Cold Spring Harbor fahoratry Laboratory Press, 1989).

The protein of the invention may be a protein whose amino acid sequence is as described under SEQ ID NO:3 or SEQ ID NO:4, or a protein having an amino acid sequence derived from the amino acid sequence shown under SEQ ID NO:3 or SEQ ID NO:4 by deletion, addition, insertion and/or substitution of one or several amino acid residues and having decaprenyl diphosphate synthase activity.

"Such an amino acid sequence derived by deletion, addition, insertion and/or substitution of one or several amino acid residues" can be obtained by deleting, adding, inserting and/or substituting an amino acid residue or residues by site-specific mutagenesis or any other methods well known in the art. Such methods are specifically described, for example, in Nucleic Acid Res., 10, 6487 (1982) and Methods in Enzymology, 100, 448 (1983).

For causing expression of the decaprenyl diphosphate synthase gene, it is necessary to connect that gene to a site downstream of an appropriate promoter. It is possible to construct an expression vector, for example, by excising a DNA fragment containing the gene using a restriction enzyme or amplifying an enzyme-encoding gene portion alone by PCR and then inserting the fragment or amplification product into a promoter-containing vector.

In the practice of the invention, the vector in which a DNA encoding a protein having decaprenyl diphosphate synthase activity is to be inserted to give an expression vector is not particularly restricted but may be one derived from an *Escherichia coli*-derived plasmid with an appropriate promoter inserted therein. The *Escherichia coli*-derived plasmid includes, among others, pBR322, pBR325, pUC19, pUC18 and pUC119, and the promoter includes, among others, the T7 promoter, trp promoter, tac promoter, lac promoter, and λPL promoter.

In the practice of the invention, pGEX-2T, pGEX-3T, pGEX-3X (the three being products of Pharmacia), pBluescriptII, pUC19, pUC18 (product of Toyobo Co., Ltd.), pMALC2, pET-3T, pUCNT (described in Publication WO 94/03613) and the like may also be used as vectors for expression. Among these, pUCNT and pUC18 are judiciously used. In specific examples, a decaprenyl diphosphate synthase gene expression vector, pNTL1, can be constructed by inserting a gene containing the DNA sequence shown under SEQ ID NO:1 into the vector for expression pUCNT, and an expression vector of decaprenyl diphosphate synthase gene, pUCA1, can be constructed when a gene containing the DNA sequence shown under SEQ ID NO:2 is inserted into the vector for expression pUC18.

And, by introducing the above enzyme gene expression vector into an appropriate microorganism, it becomes possible to utilize the microorganism for the production of coenzyme $Q_{10}$. The host microorganism is not particularly restricted but *Escherichia coli* is judiciously used. The *Escherichia coli* strain is not particularly restricted but includes XL1-Blue, BL-21, JM109, NM522, DH5α, HB101, and DH5, among others. Among these, *Escherichia coli* DH5α and JM109 are judiciously used. For example, when the decaprenyl diphosphate synthase gene expression vector pNTL1 is introduced into *Escherichia coli*, this can be transformed so that coenzyme $Q_{10}$, which *Escherichia coli* originally does not produce, can be produced. The *Escherichia coli* strain *E. coli* DH5α (pNTL1) has been deposited with the National Institute of Advanced Industrial Science and Technology International Patent Organism Depositary (zip code: 305-8566 Central 6, 1-1-1 Higashi, Tsukuba, Ibaraki, Japan) under the designation FERM BP-7353. Further, when the decaprenyl diphosphate synthase gene expression vector pUCA1 is introduced into *Escherichia coli*, this can be transformed so that coenzyme $Q_{10}$, which *Escherichia coli* originally does not produce, can be produced. The *Escherichia coli* strain *E. coli* JM109 (pUCA1) has been deposited with the National Institute of Advanced Industrial Science and Technology International Patent Organism Depositary (zip code: 305-8566 Central 6, 1-1-1 Higashi, Tsukuba, Ibaraki, Japan) under the designation FERM BP-7352.

Coenzyme $Q_{10}$ can be produced by cultivating the transformant obtained in the invention in the conventional manner and recovering coenzyme $Q_{10}$ from the cultivation product. In cases where the host microorganism is *Escherichia coli*, LB medium, or M9 medium containing glucose and casamino acids can be used as the medium. For better promoter functioning, such an agent as isopropylthiogalactoside or indolyl-3-acrylic acid, for instance, may be added to the medium. The cultivation is carried out, for example, at 37° C. for 17 to 24 hours, if necessary with aeration and/or agitation.

In the practice of the invention, the product coenzyme $Q_{10}$ obtained may be purified or used in the form of a crude product according to the selection duly made depending on the intended use thereof. Coenzyme $Q_{10}$ can be isolated from the cultivation product by an appropriate combination of per se known methods of separation and/or purification. The per se known methods of separation and/or purification include salting out, solvent precipitation and other methods utilizing the difference in solubility, dialysis, ultrafiltration, gel filtration, (SDS-)polyacrylamide gel electrophoresis and other methods mainly utilizing the difference in molecular weight, ion exchange chromatography and other methods utilizing the difference in charge, affinity chromatography and other methods utilizing specific affinity, reversed phase high-performance liquid chromatography and other methods utilizing the difference in hydrophobicity, isoelectric focusing and other methods utilizing the difference in isoelectric point, among others.

The field of utilization of coenzyme $Q_{10}$ obtained in the present invention is not particularly restricted but it may be judiciously used as a drug, among others.

DETAILED DESCRIPTION

EXAMPLE 1

Figure 1:
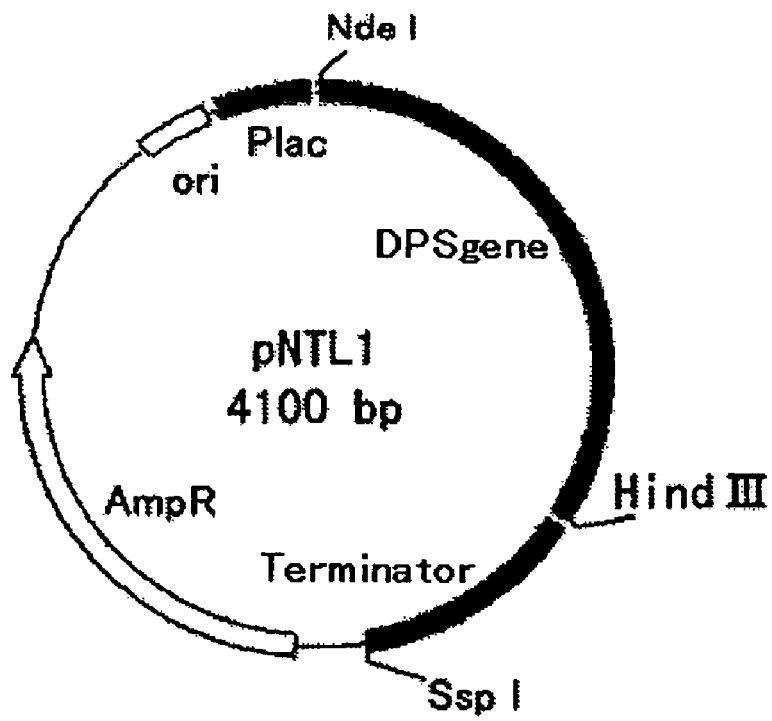
FIG. 1 is a restriction enzyme map of the expression vector pNTL1.

The chromosomal DNAs of *Leucosporidium scotti* IFO 1212 and *Aspergillus clavatus* JCM 1718 were prepared by the method of C. S. Hoffman et al. (Gene, 57 (1987), 267-272). Based on the homology with the known long-chain prenyl diphosphate synthase gene, primers for use in PCR, namely DPS-1 (SEQ ID NO:5 in the sequence listing) and DPS-1 1AS (SEQ ID NO:6 in the sequence listing), were designed. Using these, a PCR cycle of 94° C., 1 minute→43° C., 2 minutes→72° C., 2 minutes, were repeated 40 times after 3 minutes of heat treatment at 94° C., followed by 1.2% agarose gel electrophoresis.

The thus-obtained fragment, about 220 bp in size, was purified by excising the corresponding gel portion from the gel and then treating with a DNA extraction kit (Sephaglas (trademark) BrandPrep Kit, product of Amersham Pharmacia Biotech), and the purified fragment was cloned into a vector for expression in *Escherichia coli* using a PCR product direct cloning kit (pT7 BlueT-Vector Kit, product of NOVAGEN) to give pT7-L1DPS and pT7-A1DPS. The DNA base sequence was determined by carrying out the reaction on a DNA sequencer (model 377, product of PerkinElmer) using a DNA sequencing kit (product of PerkinElmer, ABI PRISM (trademark) BigDye (trademark) Terminator Cycle Sequence Ready Reaction Kit with AmptiTaq (registered trademark) DNA polymerase, FS) and according to the manual attached thereto. As a result, a DNA fragment having a base sequence covering the 709th to 915th bases of the base sequence shown under SEQ ID NO:1 in the sequence listing was obtained from *Leucosporidium scotti* IFO 1212, and a DNA fragment having a base sequence covering the 616th to 822nd bases of the base sequence shown under SEQ ID NO:2 in the sequence listing was obtained from *Aspergillus clavatus* JCM 1718, respectively. These DNA fragments were estimated to be part of the decaprenyl diphosphate synthase gene since the amino acid sequence "GDFLLXRA" (X is A or G), which is a characteristic region of the long-chain prenyl chain-containing prenyl diphosphate synthase, could be found in the sequence translated from the base sequence determined in the above manner.

EXAMPLE 2

*Leucosporidium scotti* IFO 1212 and *Aspergillus clavatus* JCM 1718 were cultured in 50 mL of 703 medium (5 g/L pepton, 3 g/L yeast extract, 3 g/L malt extract, and 1 g/L glucose, pH 6.0) for 48 hours at 25° C. Then, the cells were harvested by centrifugation at 3,000 revolutions for 20 minutes and frozen immediately in liquid nitrogen.

The frozen cells were placed in a mortar chilled previously at −70° C. and ground to a powder with a pestle while being kept frozen by occasionally adding liquid nitrogen. Total RNA was prepared from the well-powdered cells using an RNeasy Maxi RNA Purification Kit (product of Qiagen K.K.). Total RNA thus extracted was further purified using an RNeasy Mini RNA Purification Kit (product of Qiagen K.K.). From the purified total RNA, mRNA was prepared using an mRNA purification kit (Ologotex-dT30 <Super> (trademark) mRNA Purification kit, product of Takara Shuzo Co., Ltd.).

EXAMPLE 3

The DNA fragment containing the region from the DNA obtained in Example 1 to the 3'-terminal region of the decaprenyl diphosphate synthase gene of *Leucosporidium scotti* IFO 1212 was obtained. RT-PCR was carried out using an RT-PCR kit (High fidelity RNA PCR Kit, product of Takara Shuzo Co., Ltd.) and primer L1S (SEQ ID NO:7 in the sequence listing), which was generated based on the internal sequence of the DNA fragment obtained in Example 1. The thus-obtained fragment, about 850 bp in size, was purified by excising the corresponding gel portion from the gel and then treating with a DNA extraction kit (Sephaglas (trademark) BrandPrep Kit, product of Amersham Pharmacia Biotech), and the purified fragment was cloned into a vector for expression in *Escherichia coli* using a PCR product direct cloning kit (pT7 BlueT-Vector Kit, product of NOVAGEN) to give pT7-L2DPS. The DNA base sequence was determined by carrying out the reaction on a DNA sequencer (model 377, product of PerkinElmer) using a DNA sequencing kit (product of PerkinElmer, ABI PRISM (trademark) BigDye (trademark) Terminator Cycle Sequence Ready Reaction Kit With AmptiTaq (registered trademark) DNA polymerase, FS) and according to the manual attached thereto.

EXAMPLE 4

The DNA fragment containing the region from the DNA obtained in Example 1 to the 5'-terminal region of the decaprenyl diphosphate synthase gene of *Leucosporidium scotti* IFO 1212 was obtained. Reverse transcription was carried out using a 5'-Full RACE Core Set (product of Takara Shuzo Co., Ltd.), the mRNA prepared in Example 2 as template, and primer L7ASP (SEQ ID NO:8 in the sequence listing, "5'-terminal region-phosphorylated"), which was generated based on the internal sequence of the DNA fragment obtained in Example 3, to synthesize a cDNA encoding the 5'-terminal region of the gene containing a part of the fragment obtained in Example 3. Then, the cDNA was circularized using the above kit.

PCR was carried out using this circularized cDNA as template, and primers L5S (SEQ ID NO:9 in the sequence listing) and L4AS (SEQ ID NO:10 in the sequence listing), which were generated based on the known part of the sequence obtained in Example 3. Furthermore, PCR was carried out to the PCR product using primers L6S (SEQ ID NO:11 in the sequence listing) and L3AS (SEQ ID NO:12 in the sequence listing) to obtain a fragment, about 950 bp in size. The thus-obtained fragment, about 950 bp in size, was purified by excising the corresponding gel portion from the gel and then treating with a DNA extraction kit (Sephaglas (trademark) BrandPrep Kit, product of Amersham Pharmacia Biotech), and the purified fragment was cloned into a vector for expression in *Escherichia coli* using a PCR product direct cloning kit (pT7 BlueT-Vector Kit, product of NOVAGEN) to give pT7-L3DPS. The DNA base sequence was determined by carrying out the reaction on a DNA sequencer (model 377, product of PerkinElmer) using a DNA sequencing kit (product of PerkinElmer, ABI PRISM (trademark) BigDye (trademark) Terminator Cycle Sequence Ready Reaction Kit With AmptiTaq (registered trademark) DNA polymerase, FS) and according to the manual attached thereto.

EXAMPLE 5

To obtain the full-length sequence of the decaprenyl diphosphate synthase gene of *Leucosporidium scotti* IFO 1212, PCR was carried out using pT7-L3DPS as template, primer LN1-2 (SEQ ID NO:13 in the sequence listing), which was generated based on the 5'-terminal sequence of the gene and primer L3AS (SEQ ID NO:12 in the sequence listing) described above to obtain the 5'-terminal region, about 700 bp in size. And, PCR was carried out using pT7-L2DPS as template, primer L1S (SEQ ID NO:7 in the sequence listing) described above and primer LCH (SEQ ID NO:14 in the sequence listing), which was generated based on the 3'-terminal sequence of the gene, to obtain the 3'-terminal region, about 770 bp in size. The two fragments were mixed and denatured, and then slowly cooled to allow annealing, followed by duplex synthesis using DNA polymerase. Subsequently, PCR was carried out using the double-stranded DNA as template, and primers LN1-2 and LCH to obtain DNA containing the full-length sequence of the gene. The base sequence was determined using a DNA sequencer (model 377, product of PerkinElmer, Inc.) and a DNA sequencing kit (product of PerkinElmer, Inc., ABI PRISM (trademark) BigDye (trademark) Terminator Cycle Sequence Ready Reaction Kit With AmptiTaq (registered trademark) DNA polymerase, FS) and according to the manual attached thereto. Thus, the total sequence of the decaprenyl diphosphate synthase gene of *Leucosporidium scotti* IFO 1212 was revealed. Base sequence was determined on the DNA, about 1.5 kbp in size, and the result is shown under SEQ ID NO:1 in the sequence listing. The amino acid sequence deduced from this base sequence is shown under SEQ ID NO:3.

EXAMPLE 6

The DNA obtained in Example 5 was cleaved with the restriction enzymes NdeI and HindIII, and the cleavage product was inserted into a vector for expression, pUCNT (described in WO 94/03613), to give a decaprenyl diphosphate synthase gene expression vector, pNTL1. The restriction enzyme map of the thus-obtained expression vector pNTL1 is shown in FIG. 1. The symbol DPS stands for the coding region of the decaprenyl diphosphate synthase gene.

EXAMPLE 7

The DNA fragment containing the region from the DNA fragment obtained in Example 1 to the 3'-terminal region of the decaprenyl diphosphate synthase gene of *Aspergillus clavatus* JCM 1718 was obtained. RT-PCR was carried out using an RT-PCR kit (High fidelity RNA PCR Kit, product of Takara Shuzo Co., Ltd.) and primer A1S (SEQ ID NO:15 in the sequence listing), which was generated based on the internal sequence of the DNA fragment obtained in Example 1. The thus-obtained fragment, about 850 bp in size, was purified by excising the corresponding gel portion from the gel and then treating with a DNA extraction kit (Sephaglas (trademark) BrandPrep Kit, product of Amersham Pharmacia Biotech), and the purified fragment was cloned into a vector for expression in *Escherichia coli* using a PCR product direct cloning kit (pT7 BlueT-Vector Kit, product of NOVAGEN) to give pT7-A2DPS. The DNA base sequence was determined by carrying out the reaction on a DNA sequencer (model 377, product of PerkinElmer) using a DNA sequencing kit (product of PerkinElmer, ABI PRISM (trademark) BigDye (trademark) Terminator Cycle Sequence Ready Reaction Kit With AmptiTaq (registered trademark) DNA polymerase, FS) and according to the manual attached thereto.

EXAMPLE 8

The DNA fragment containing the region from the DNA fragment obtained in Example 1 to the 5'-terminal region of the decaprenyl diphosphate synthase gene of *Aspergillus clavatus* JCM 1718 was obtained. Reverse transcription was carried out using a 5'-Full RACE Core Set (product of Takara Shuzo Co., Ltd.), the mRNA prepared in Example 2 as template, and primer A7ASP (SEQ ID NO:16 in the sequence listing, "5'-terminal region-phosphorylated"), which was generated based on the internal sequence of the DNA fragment obtained in Example 7 to synthesize a cDNA encoding the 5'-terminal region of the gene containing a part of the fragment obtained in Example 7. Then, the cDNA was circularized using the above kit.

PCR was carried out using this circularized cDNA as template, and primers A5S (SEQ ID NO:17 in the sequence listing) and A2AS (SEQ ID NO:18 in the sequence listing), which were generated based on the known part of the sequence obtained in Example 3. Furthermore, PCR was carried out to the PCR product using primers A6S (SEQ ID NO:19 in the sequence listing) and A3AS (SEQ ID NO:20 in the sequence listing) to obtain a fragment, about 850 bp in size. The thus-obtained fragment was purified by excising the corresponding gel portion from the gel and then treating with a DNA extraction kit (Sephaglas (trademark) BrandPrep Kit, product of Amersham Pharmacia Biotech), and the purified fragment was cloned into a vector for expression in *Escherichia coli* using a PCR product direct cloning kit (pT7 BlueT-Vector Kit, product of NOVAGEN) to give pT7-A3DPS. The DNA base sequence was determined by carrying out the reaction on a DNA sequencer (model 377, product of PerkinElmer) using a DNA sequencing kit (product of PerkinElmer, ABI PRISM (trademark) BigDye (trademark) Terminator Cycle Sequence Ready Reaction Kit With AmptiTaq (registered trademark) DNA polymerase, FS) and according to the manual attached thereto.

EXAMPLE 9

To obtain the full-length sequence of the decaprenyl diphosphate synthase gene of *Aspergillus clavatus* JCM 1718, PCR was carried out using pT7-A3DPS as template, primer AN2 (SEQ ID NO:21 in the sequence listing), which was generated based on the 5'-terminal sequence of the gene and primer A3AS (SEQ ID NO:20 in the sequence listing) described above to obtain the 5'-terminal region, about 700 bp in size. And, PCR was carried out using pT7-L2DPS as template, primer A1S (SEQ ID NO:15 in the sequence listing) described above and primer ACH (SEQ ID NO:22 in the sequence listing), which was generated based on the 3'-terminal sequence of the gene, to obtain the 3'-terminal region, about 770 bp in size.

The two fragments were mixed and denatured, and then slowly cooled to allow annealing, followed by duplex synthesis using DNA polymerase. Subsequently, PCR was carried out using the double-stranded DNA as template, and primers AN2 and ACH to obtain DNA. The base sequence was determined by carrying out the reaction on a DNA sequencer (model 377, product of PerkinElmer, Inc.) using a DNA sequencing kit (product of PerkinElmer, Inc., ABI PRISM (trademark) BigDye (trademark) Terminator Cycle Sequence Ready Reaction Kit With AmptiTaq (registered trademark) DNA polymerase, FS) and according to the manual attached thereto. Thus, the total sequence of the decaprenyl diphosphate synthase gene of *Aspergillus clavatus* JCM 1718 was revealed. Base sequence was determined on the DNA, about 1.4 kbp in size, and the result is shown under SEQ ID NO:2 in the sequence listing. The amino acid sequence deduced from this DNA sequence is shown under SEQ ID NO:4.

EXAMPLE 10

Figure 2:
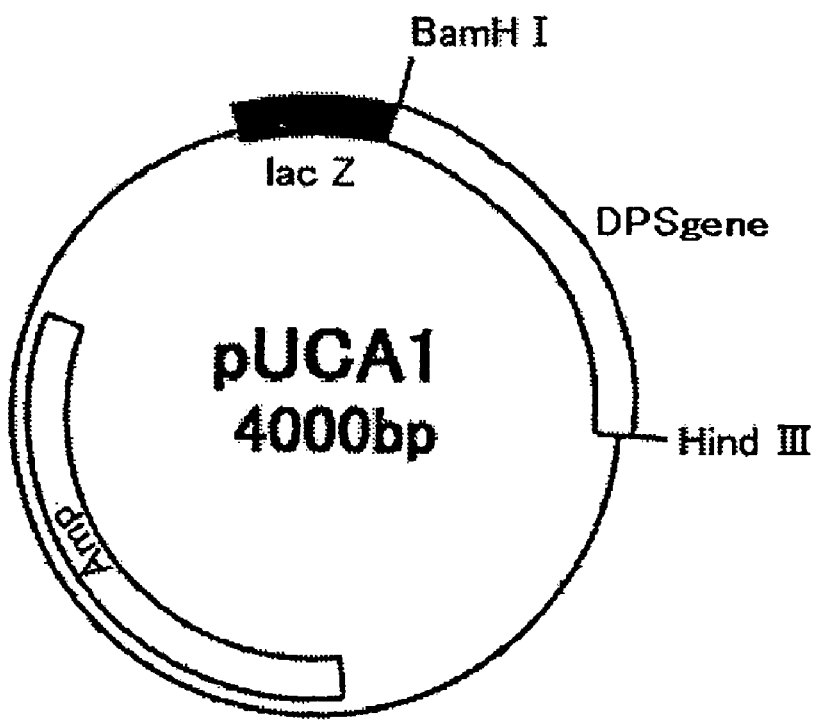
FIG. 2 is a restriction enzyme map of the expression vector pUCA1.

The DNA obtained in Example 9 was cleaved with the restriction enzymes BamHI and HindIII, and the cleavage product was inserted into a vector for expression, pUC18, to give a decaprenyl diphosphate synthase gene expression vector, pUCA1. The restriction enzyme map of the thus-obtained expression vector pUCA1 is shown in FIG. 2. The symbol DPS stands for the coding region of the decaprenyl diphosphate synthase gene.

EXAMPLE 11

The decaprenyl diphosphate synthase gene expression vector pNTL1 was introduced into *Escherichia coli* DH5α and pUCA1 was introduced into JM109, respectively, to produce recombinant *Escherichia coli*, *E. coli* DH5α (pNTL1) and *E. coli* JM109 (pUCA1). Each recombinant *Escherichia coli* was shake-cultured overnight in 10 mL of LB medium at 37° C., and cells were harvested by centrifugation (3,000 revolutions, 20 minutes).

Figure 3:
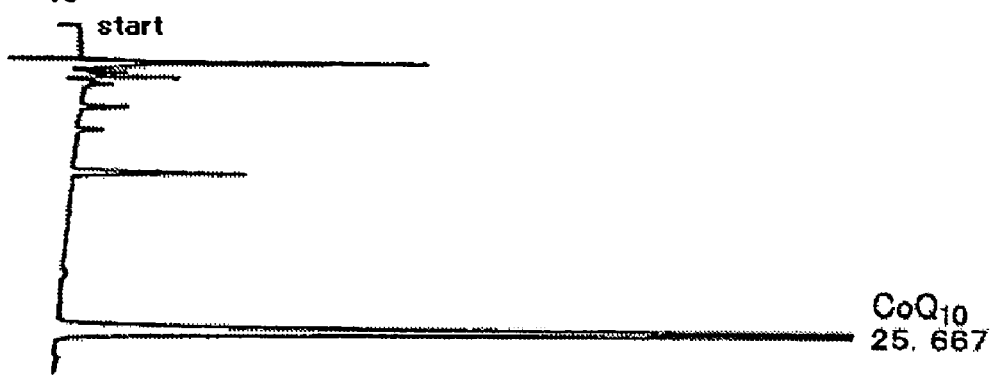
FIG. 3 shows HPLC analysis charts showing production of coenzyme $Q_{10}$ by recombinant *Escherichia coli*, *E. coli* DH5α (pNTL1).
Figure 3:
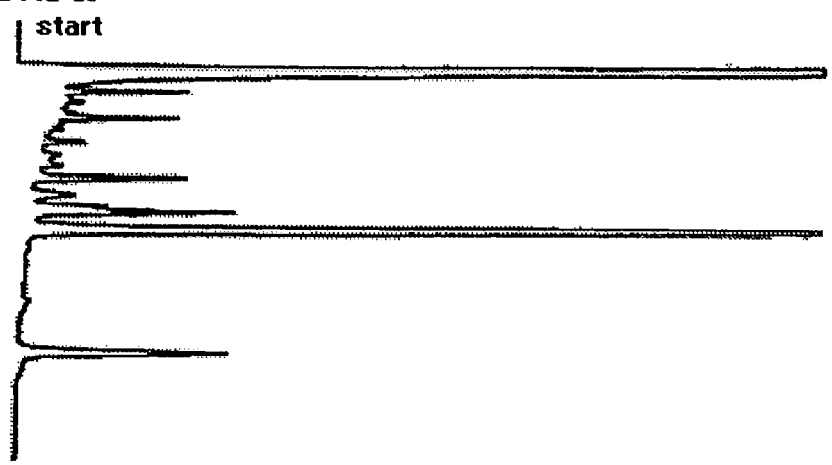
Figure 3:
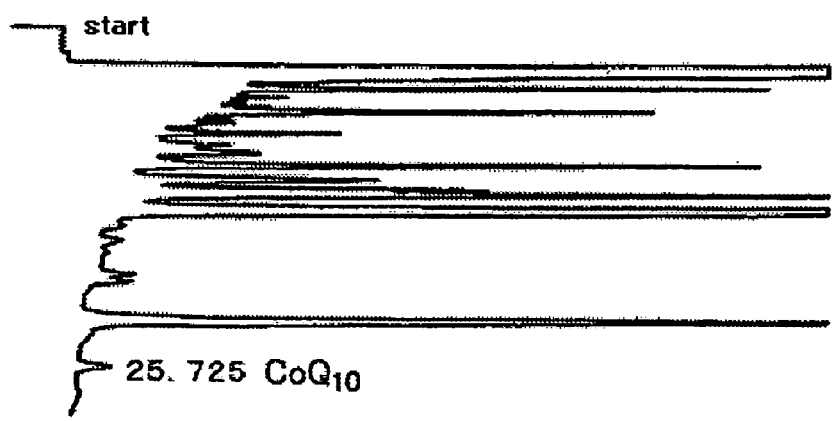
Figure 4:
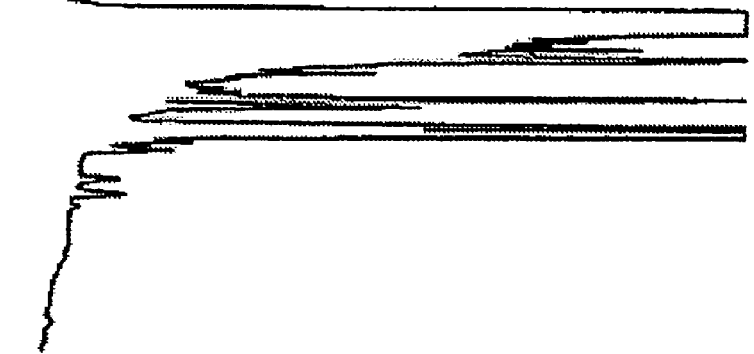
FIG. 4 shows HPLC analysis charts showing production of coenzyme $Q_{10}$ by recombinant *Escherichia coli*, *E. coli* JM109 (pUCA1).
Figure 4:
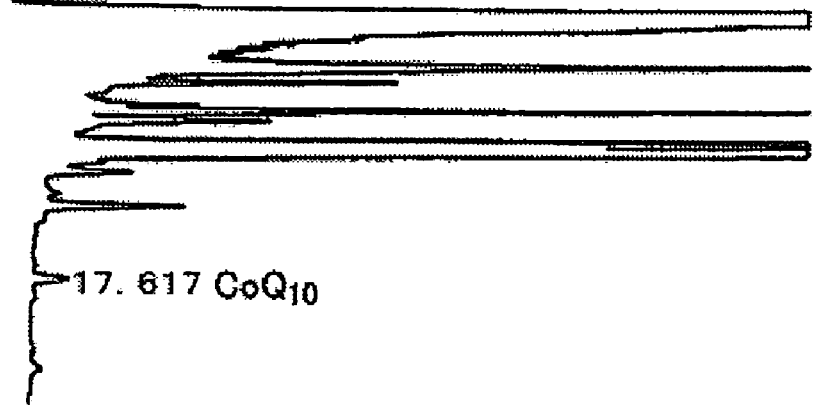

The cells were suspended in 1 mL of a 3% aqueous solution of sulfuric acid and, after 30 minutes of heat treatment at 120° C., 2 mL of a 14% aqueous solution of sodium hydroxide was added, followed by further 15 minutes of heat treatment at 120° C. To the thus-treated suspension was added 3 mL of hexane-isopropanol (10:2) for effecting extraction. After centrifugation, 1.5 mL of the organic solvent layer was separated, and the solvent was evaporated to dryness under reduced pressure conditions. The residue was dissolved in 200 μL of ethanol, and 20 μL of the solution was analyzed by high-performance liquid chromatography (using LC-10A, product of Shimadzu Corp.). For separation, a reversed phase column (YMC-pack ODS-A, 250×4.6 mm, S-5 μm, 120 A) was used, and the coenzyme $Q_{10}$ formed was detected based on the absorbance at the wavelength 275 nm. The result of *E. coli* DH5α (pNTL1) (analyzed with mobile phase: methanol/hexane=85/15) is shown in FIG. 3, and the result of *E. coli* JM109 (pUCA1) (analyzed with mobile phase: ethanol/methanol=2/1) is shown in FIG. 4. As shown in FIGS. 3 and 4, it was revealed that, upon introduction of the decaprenyl diphosphate synthase gene for expression thereof, coenzyme $Q_{10}$, which is originally not produced in *Escherichia coli*, could now be produced in recombinant *Escherichia coli*.

The thus-obtained recombinant *Escherichia coli* DH5α (pNTL1) (deposition/accession No. FERM BP-7353) and *E. coli* JM109(pUCA1) (deposition/accession No. FERM BP-7352) have been deposited, under the Budapest Treaty, with the National Institute of Advanced Industrial Science and Technology International Patent Organism Depositary (zip code: 305-8566 Central 6, 1-1-1 Higashi, Tsukuba, Ibaraki, JAPAN) as of Nov. 9, 2000.

INDUSTRIAL APPLICABILITY

A gene encoding decaprenyl diphosphate synthase, which is the key enzyme in the biosynthesis of coenzyme $Q_{10}$, was isolated from a fungal species belonging to the genus *Leucosporidium* and genus *Aspergillus* and it was sequenced. This could successfully be introduced in *Escherichia coli* for expression thereof. Furthermore, improvements in gene sequence successfully resulted in-production in significant amounts. By using the method of the invention, it becomes possible to efficiently produce coenzyme $Q_{10}$, which is in use as a drug, among others.

The invention claimed is:

1. An isolated DNA encoding a protein with an amino acid sequence as described under SEQ ID NO:4.

2. An isolated DNA whose nucleotide sequence is as described under SEQ ID NO:2.

3. An expression vector resulting from insertion of the DNA according to claim 1 into a vector for expression.

4. An expression vector resulting from insertion of the DNA according to claim 2 into a vector for expression.

5. The expression vector according to claim 4, wherein the vector for expression is pUC18.

6. A transformant resulting from transformation of a host microorganism with the DNA according to claim 2.

7. A transformant resulting from transformation of a host microorganism with the expression vector according to claim 4.

8. The transformant according to claim 6, wherein the host microorganism is a strain of *Escherichia coli*.

9. The transformant according to claim 8, wherein the strain of *Escherichia coli* is *Escherichia coli* DH5α or JM109.

10. The transformant according to claim 9, which is *E. coli* JM109 (pUCA1) (FERM BP-7352).

11. A process for producing coenzyme $Q_{10}$, which comprises cultivating the transformant according to claim 8 in a medium and recovering coenzyme $Q_{10}$ thus formed and accumulated in the medium.

* * * * *

SEQUENCE LISTING

<160> NUMBER OF SEQ ID NOS: 22

<210> SEQ ID NO 1
<211> LENGTH: 1506
<212> TYPE: DNA
<213> ORGANISM: Leucosporidium scottii

<400> SEQUENCE: 1

```
atg tcg cgg aca ctg ccg ata tct cgc ttg aga gga cgt gca cgg cca        48
Met Ser Arg Thr Leu Pro Ile Ser Arg Leu Arg Gly Arg Ala Arg Pro
  1               5                  10                  15 tct tcg agt cta cta cag ctc cca act gag ctg caa aag ctc tcc tcc        96
Ser Ser Ser Leu Leu Gln Leu Pro Thr Glu Leu Gln Lys Leu Ser Ser
             20                  25                  30 tcc cca acc tca tcc ctc cgt cat gct tcc cct tcc cgc tcc gcc tgg       144
Ser Pro Thr Ser Ser Leu Arg His Ala Ser Pro Ser Arg Ser Ala Trp
         35                  40                  45 act tca gcc atc ccc ggt ctc tcg tct gcc acc cca ttc gct tcg act       192
Thr Ser Ala Ile Pro Gly Leu Ser Ser Ala Thr Pro Phe Ala Ser Thr
     50                  55                  60 tca acc tct tcc tcc ctc ctc gct ggc tca tcc aaa gta gcg ttg caa       240
Ser Thr Ser Ser Ser Leu Leu Ala Gly Ser Ser Lys Val Ala Leu Gln
 65                  70                  75                  80 gat ccc ctc aag ccg cta ggc gca gag atg ggc ttg ctg agg tcc aac       288
Asp Pro Leu Lys Pro Leu Gly Ala Glu Met Gly Leu Leu Arg Ser Asn
                 85                  90                  95 gtc cag cac ctc ctt ggt tca ggt cat cca gca ctg gat acc atc gcc       336
Val Gln His Leu Leu Gly Ser Gly His Pro Ala Leu Asp Thr Ile Ala
            100                 105                 110 aag tac tac ttt caa gcc gaa ggg aag cat gtt cga ccg atg ctc atc       384
Lys Tyr Tyr Phe Gln Ala Glu Gly Lys His Val Arg Pro Met Leu Ile
        115                 120                 125 ttg ctc atg agc caa gcg acg aat gga ctc gca ccc ggc tgg gaa cag       432
Leu Leu Met Ser Gln Ala Thr Asn Gly Leu Ala Pro Gly Trp Glu Gln
    130                 135                 140 agg cgg gat caa gcg gca gca gcg gaa ctg aag agg gag caa ggc gac       480
Arg Arg Asp Gln Ala Ala Ala Ala Glu Leu Lys Arg Glu Gln Gly Asp
145                 150                 155                 160 gaa gga tta gga ggg gac gat atc gac gaa cct cta agc cca cct tcc       528
Glu Gly Leu Gly Gly Asp Asp Ile Asp Glu Pro Leu Ser Pro Pro Ser
```

-continued

| | | | | | | | | | | | | | | | |
|---|---|---|---|---|---|---|---|---|---|---|---|---|---|---|---|
| | | | | 165 | | | | 170 | | | | 175 | | | |
| gtc | ctc | aac | gac | caa | aac | ccc | tcg | atg | ctc | gct | tcg | gcc | aaa | tcg | ttc | 576 |
| Val | Leu | Asn | Asp | Gln | Asn | Pro | Ser | Met | Leu | Ala | Ser | Ala | Lys | Ser | Phe | |
| | | | 180 | | | | | 185 | | | | | 190 | | | |

| ttc | tcc | gac | cct | ctc | gct | tcg | ctc | cga | ccc | gct | ccc | act | ccc | act | tcc | 624 |
|---|---|---|---|---|---|---|---|---|---|---|---|---|---|---|---|---|
| Phe | Ser | Asp | Pro | Leu | Ala | Ser | Leu | Arg | Pro | Ala | Pro | Thr | Pro | Thr | Ser | |
| | | 195 | | | | | 200 | | | | | 205 | | | | |

| atc | gcc | caa | tca | atc | cat | caa | act | cac | ctc | ctt | ccc | tcc | caa | cgt | cgt | 672 |
|---|---|---|---|---|---|---|---|---|---|---|---|---|---|---|---|---|
| Ile | Ala | Gln | Ser | Ile | His | Gln | Thr | His | Leu | Leu | Pro | Ser | Gln | Arg | Arg | |
| 210 | | | | | 215 | | | | | 220 | | | | | | |

| ctc | gcc | gaa | atc | acc | gaa | atg | att | cac | gtc | gcc | tcg | ttg | ctg | cac | gac | 720 |
|---|---|---|---|---|---|---|---|---|---|---|---|---|---|---|---|---|
| Leu | Ala | Glu | Ile | Thr | Glu | Met | Ile | His | Val | Ala | Ser | Leu | Leu | His | Asp | |
| 225 | | | | | 230 | | | | | 235 | | | | | 240 | |

| gat | gtt | att | gac | ctc | gca | gag | acg | agg | cga | tcg | gcc | ccc | tca | gct | cct | 768 |
|---|---|---|---|---|---|---|---|---|---|---|---|---|---|---|---|---|
| Asp | Val | Ile | Asp | Leu | Ala | Glu | Thr | Arg | Arg | Ser | Ala | Pro | Ser | Ala | Pro | |
| | | | | 245 | | | | | 250 | | | | | 255 | | |

| tcg | ctc | ttt | ggc | aac | aag | ctc | tcc | atc | ctc | gcg | gga | gat | ttc | ttg | ctc | 816 |
|---|---|---|---|---|---|---|---|---|---|---|---|---|---|---|---|---|
| Ser | Leu | Phe | Gly | Asn | Lys | Leu | Ser | Ile | Leu | Ala | Gly | Asp | Phe | Leu | Leu | |
| | | | 260 | | | | | 265 | | | | | 270 | | | |

| gcc | cga | gct | tcc | ctc | gct | ctc | tcg | agg | ttg | ggg | agc | aat | gag | gta | gtc | 864 |
|---|---|---|---|---|---|---|---|---|---|---|---|---|---|---|---|---|
| Ala | Arg | Ala | Ser | Leu | Ala | Leu | Ser | Arg | Leu | Gly | Ser | Asn | Glu | Val | Val | |
| | | 275 | | | | | 280 | | | | | 285 | | | | |

| gag | ctc | gtc | gct | tcc | gtt | ctc | gcc | aac | ttg | gtc | gag | ggg | gag | gtt | atg | 912 |
|---|---|---|---|---|---|---|---|---|---|---|---|---|---|---|---|---|
| Glu | Leu | Val | Ala | Ser | Val | Leu | Ala | Asn | Leu | Val | Glu | Gly | Glu | Val | Met | |
| 290 | | | | | 295 | | | | | 300 | | | | | | |

| cag | atg | aag | ggg | aac | gta | ccg | ggc | aag | gaa | ggg | ctg | ttg | gca | ggg | gca | 960 |
|---|---|---|---|---|---|---|---|---|---|---|---|---|---|---|---|---|
| Gln | Met | Lys | Gly | Asn | Val | Pro | Gly | Lys | Glu | Gly | Leu | Leu | Ala | Gly | Ala | |
| 305 | | | | | 310 | | | | | 315 | | | | | 320 | |

| gga | gga | gga | tca | aca | gcc | aag | gga | ccg | aca | ccc | gag | atc | ttc | gac | cac | 1008 |
|---|---|---|---|---|---|---|---|---|---|---|---|---|---|---|---|---|
| Gly | Gly | Gly | Ser | Thr | Ala | Lys | Gly | Pro | Thr | Pro | Glu | Ile | Phe | Asp | His | |
| | | | | 325 | | | | | 330 | | | | | 335 | | |

| tac | atg | aag | aag | acg | tac | ctc | aag | acg | gcg | agc | ctg | att | gcc | aaa | agt | 1056 |
|---|---|---|---|---|---|---|---|---|---|---|---|---|---|---|---|---|
| Tyr | Met | Lys | Lys | Thr | Tyr | Leu | Lys | Thr | Ala | Ser | Leu | Ile | Ala | Lys | Ser | |
| | | | 340 | | | | | 345 | | | | | 350 | | | |

| acg | agg | gcg | acg | acg | att | cta | ggt | gga | tgt | gga | gtc | aag | cag | gga | tgg | 1104 |
|---|---|---|---|---|---|---|---|---|---|---|---|---|---|---|---|---|
| Thr | Arg | Ala | Thr | Thr | Ile | Leu | Gly | Gly | Cys | Gly | Val | Lys | Gln | Gly | Trp | |
| | | 355 | | | | | 360 | | | | | 365 | | | | |

| gca | gag | gga | gag | aag | gtc | aag | gat | atc | gcc | tac | tcg | tat | ggt | cgt | aac | 1152 |
|---|---|---|---|---|---|---|---|---|---|---|---|---|---|---|---|---|
| Ala | Glu | Gly | Glu | Lys | Val | Lys | Asp | Ile | Ala | Tyr | Ser | Tyr | Gly | Arg | Asn | |
| 370 | | | | | 375 | | | | | 380 | | | | | | |

| ttg | ggc | atc | gcc | ttc | cag | ctc | gtg | gac | gac | atg | ctc | gac | ttt | acg | gca | 1200 |
|---|---|---|---|---|---|---|---|---|---|---|---|---|---|---|---|---|
| Leu | Gly | Ile | Ala | Phe | Gln | Leu | Val | Asp | Asp | Met | Leu | Asp | Phe | Thr | Ala | |
| 385 | | | | | 390 | | | | | 395 | | | | | 400 | |

| tca | gca | gca | caa | ctc | ggc | aaa | cca | gga | gga | gga | gcc | gac | ctc | aaa | ctc | 1248 |
|---|---|---|---|---|---|---|---|---|---|---|---|---|---|---|---|---|
| Ser | Ala | Ala | Gln | Leu | Gly | Lys | Pro | Gly | Gly | Gly | Ala | Asp | Leu | Lys | Leu | |
| | | | | 405 | | | | | 410 | | | | | 415 | | |

| ggt | ctc | gct | acc | gca | cca | gca | ctc | tac | gcg | tgg | gag | gaa | ttc | ccc | gaa | 1296 |
|---|---|---|---|---|---|---|---|---|---|---|---|---|---|---|---|---|
| Gly | Leu | Ala | Thr | Ala | Pro | Ala | Leu | Tyr | Ala | Trp | Glu | Glu | Phe | Pro | Glu | |
| | | | 420 | | | | | 425 | | | | | 430 | | | |

| ttg | ggg | gcg | atg | att | gag | cgc | aag | ttt | gct | ggc | gag | gac | gat | gtc | gag | 1344 |
|---|---|---|---|---|---|---|---|---|---|---|---|---|---|---|---|---|
| Leu | Gly | Ala | Met | Ile | Glu | Arg | Lys | Phe | Ala | Gly | Glu | Asp | Asp | Val | Glu | |
| | | 435 | | | | | 440 | | | | | 445 | | | | |

| cag | gcc | cga | cac | ctc | atc | tcg | cgc | tcc | tcc | ggg | gcc | gaa | cga | acg | gcc | 1392 |
|---|---|---|---|---|---|---|---|---|---|---|---|---|---|---|---|---|
| Gln | Ala | Arg | His | Leu | Ile | Ser | Arg | Ser | Ser | Gly | Ala | Glu | Arg | Thr | Ala | |
| 450 | | | | | 455 | | | | | 460 | | | | | | |

| gct | ctc | gcc | gcc | gag | cac | tca | aaa | ttg | gcg | cgt | caa | gcg | ctc | gaa | ggt | 1440 |
|---|---|---|---|---|---|---|---|---|---|---|---|---|---|---|---|---|
| Ala | Leu | Ala | Ala | Glu | His | Ser | Lys | Leu | Ala | Arg | Gln | Ala | Leu | Glu | Gly | |
| 465 | | | | | 470 | | | | | 475 | | | | | 480 | |

| ctc | ccc | gat | agc | gag | gcg | agg | aca | gca | ttg | gat | aac | atg | gcg | agg | gat | 1488 |

```
                Leu Pro Asp Ser Glu Ala Arg Thr Ala Leu Asp Asn Met Ala Arg Asp
                                485                 490                 495 aca ttg tcg agg aag aag                                                             1506
Thr Leu Ser Arg Lys Lys
                500

<210> SEQ ID NO 2
<211> LENGTH: 1353
<212> TYPE: DNA
<213> ORGANISM: Aspergillus clavatus

<400> SEQUENCE: 2 atg aga gct cga acg gtc tcg gcc tct ggc ctc att ctc tca tcg cga            48
Met Arg Ala Arg Thr Val Ser Ala Ser Gly Leu Ile Leu Ser Ser Arg
 1               5                  10                  15 acg acg acc tcg acc tcg ata tgc tgg caa tgc ctt cgt gaa gat ctc            96
Thr Thr Thr Ser Thr Ser Ile Cys Trp Gln Cys Leu Arg Glu Asp Leu
                20                  25                  30 ctc tca aat caa gtt caa atc cac gtt cga aaa tac cat ccc acc cgc           144
Leu Ser Asn Gln Val Gln Ile His Val Arg Lys Tyr His Pro Thr Arg
            35                  40                  45 cgg aaa gat gtc tct ccc ttc ggt gcc gcc gtt tct gca gcg cag acc           192
Arg Lys Asp Val Ser Pro Phe Gly Ala Ala Val Ser Ala Ala Gln Thr
        50                  55                  60 atc ttc aaa ggc ctg cca aag gct cct ccg ggg atc tcg gta gat cca           240
Ile Phe Lys Gly Leu Pro Lys Ala Pro Pro Gly Ile Ser Val Asp Pro
 65                 70                  75                  80 ttg agg atc gtg ggg aaa gag ctc aag ttt ttg acg aag aat ata cgc           288
Leu Arg Ile Val Gly Lys Glu Leu Lys Phe Leu Thr Lys Asn Ile Arg
                85                  90                  95 caa ttg ctg ggt tcg ggc cac ccg act ctt gat aaa gtg gcc aaa tat           336
Gln Leu Leu Gly Ser Gly His Pro Thr Leu Asp Lys Val Ala Lys Tyr
            100                 105                 110 tac acc cgc agc gag ggc aaa cat atg cgt ccg ctt ttg gtc ctg ctc           384
Tyr Thr Arg Ser Glu Gly Lys His Met Arg Pro Leu Leu Val Leu Leu
        115                 120                 125 atg tca cag gcg acg gcg ttg act ccg cgg cag agt cgt tca aac ttc           432
Met Ser Gln Ala Thr Ala Leu Thr Pro Arg Gln Ser Arg Ser Asn Phe
130                 135                 140 acc cct tca cag atg gtc aat gat ccc att agc tcg cct tcc gtc ctc           480
Thr Pro Ser Gln Met Val Asn Asp Pro Ile Ser Ser Pro Ser Val Leu
145                 150                 155                 160 gcc gat acg aac ccg gat ctc agc ccg ctt gtc tcg aaa tcg gcc gaa           528
Ala Asp Thr Asn Pro Asp Leu Ser Pro Leu Val Ser Lys Ser Ala Glu
                165                 170                 175 gcg caa tat gat ttt gcg ggg gat gag aat acc ctg cct acg cag cgc           576
Ala Gln Tyr Asp Phe Ala Gly Asp Glu Asn Thr Leu Pro Thr Gln Arg
            180                 185                 190 cga ctc gct gag atc acg gaa ttg atc cat acc gcc tcg ctc ctc cac           624
Arg Leu Ala Glu Ile Thr Glu Leu Ile His Thr Ala Ser Leu Leu His
        195                 200                 205 gac gac gtg atc gac aac gct gtt act cgg agg tcg tct aac tcc gca           672
Asp Asp Val Ile Asp Asn Ala Val Thr Arg Arg Ser Ser Asn Ser Ala
210                 215                 220 aac ctc cag ttt gga aat aag atg gcc gtc ctg gcc gga gat ttc ctg           720
Asn Leu Gln Phe Gly Asn Lys Met Ala Val Leu Ala Gly Asp Phe Leu
225                 230                 235                 240 ctc ggc cga gct tcc gtc gcc ctg gcg cgc ctg aga gac ccc gag gtc           768
Leu Gly Arg Ala Ser Val Ala Leu Ala Arg Leu Arg Asp Pro Glu Val
                245                 250                 255
```

|  |  |  |  |  |  |  |  |  |  |  |  |  |  |  |  | |
|---|---|---|---|---|---|---|---|---|---|---|---|---|---|---|---|---|
| aca | gaa | ctg | ctt | gca | act | gtc | att | gcc | aac | ctg | gtg | gag | gga | gag | ttc | 816 |
| Thr | Glu | Leu | Leu | Ala | Thr | Val | Ile | Ala | Asn | Leu | Val | Glu | Gly | Glu | Phe | |
|  |  | 260 |  |  |  |  | 265 |  |  |  |  | 270 |  |  |  | |
| atg | caa | ttg | aag | aat | acc | gcc | gcg | gat | gag | aag | aac | ccc | gtg | ttc | acc | 864 |
| Met | Gln | Leu | Lys | Asn | Thr | Ala | Ala | Asp | Glu | Lys | Asn | Pro | Val | Phe | Thr | |
|  | 275 |  |  |  |  | 280 |  |  |  |  | 285 |  |  |  |  | |
| gac | ggg | acc | atc | tcg | tac | tac | ttg | caa | aag | acg | tac | ctc | aag | acc | gcc | 912 |
| Asp | Gly | Thr | Ile | Ser | Tyr | Tyr | Leu | Gln | Lys | Thr | Tyr | Leu | Lys | Thr | Ala | |
|  | 290 |  |  |  |  | 295 |  |  |  |  | 300 |  |  |  |  | |
| agt | ctg | atc | agc | aag | tcg | tgc | cgt | gca | gcg | gca | tta | cta | ggt | ggc | agt | 960 |
| Ser | Leu | Ile | Ser | Lys | Ser | Cys | Arg | Ala | Ala | Ala | Leu | Leu | Gly | Gly | Ser | |
| 305 |  |  |  |  | 310 |  |  |  |  | 315 |  |  |  |  | 320 | |
| acg | cct | gag | gtt | gtc | gat | gct | gct | tat | gcc | tat | gga | cgc | aac | ctg | ggc | 1008 |
| Thr | Pro | Glu | Val | Val | Asp | Ala | Ala | Tyr | Ala | Tyr | Gly | Arg | Asn | Leu | Gly | |
|  |  |  | 325 |  |  |  |  | 330 |  |  |  |  | 335 |  |  | |
| ctg | gca | ttc | cag | ctg | gtg | gat | gat | ctg | ctg | gat | tac | acc | gtg | agt | ggg | 1056 |
| Leu | Ala | Phe | Gln | Leu | Val | Asp | Asp | Leu | Leu | Asp | Tyr | Thr | Val | Ser | Gly | |
|  |  |  | 340 |  |  |  |  | 345 |  |  |  |  | 350 |  |  | |
| gtt | gag | tta | ggc | aag | cct | gcc | gga | gcc | gat | ctg | gag | ctg | ggt | ctt | gcg | 1104 |
| Val | Glu | Leu | Gly | Lys | Pro | Ala | Gly | Ala | Asp | Leu | Glu | Leu | Gly | Leu | Ala | |
|  |  | 355 |  |  |  |  | 360 |  |  |  |  | 365 |  |  |  | |
| act | gct | ccg | ctg | ctc | ttt | gcc | tgg | aag | cag | aac | cct | gag | ctg | ggc | ccc | 1152 |
| Thr | Ala | Pro | Leu | Leu | Phe | Ala | Trp | Lys | Gln | Asn | Pro | Glu | Leu | Gly | Pro | |
|  | 370 |  |  |  |  | 375 |  |  |  |  | 380 |  |  |  |  | |
| ttg | gtc | ggt | cgg | aag | ttc | agc | cga | gag | ggg | gat | gta | caa | atg | gct | cgt | 1200 |
| Leu | Val | Gly | Arg | Lys | Phe | Ser | Arg | Glu | Gly | Asp | Val | Gln | Met | Ala | Arg | |
| 385 |  |  |  |  | 390 |  |  |  |  | 395 |  |  |  |  | 400 | |
| gaa | ctg | gtg | tac | aag | agc | gat | ggc | gtt | gaa | cag | acc | cgc | gct | ctg | gcc | 1248 |
| Glu | Leu | Val | Tyr | Lys | Ser | Asp | Gly | Val | Glu | Gln | Thr | Arg | Ala | Leu | Ala | |
|  |  |  |  | 405 |  |  |  |  | 410 |  |  |  |  | 415 |  | |
| cag | gag | tac | gcc | gac | aag | gcc | att | acc | gcc | gtc | agc | aac | ttc | cct | gac | 1296 |
| Gln | Glu | Tyr | Ala | Asp | Lys | Ala | Ile | Thr | Ala | Val | Ser | Asn | Phe | Pro | Asp | |
|  |  | 420 |  |  |  |  | 425 |  |  |  |  | 430 |  |  |  | |
| agt | gaa | gcc | aag | gct | ggt | ctc | atc | caa | atg | tgc | gag | aaa | gcc | atg | aac | 1344 |
| Ser | Glu | Ala | Lys | Ala | Gly | Leu | Ile | Gln | Met | Cys | Glu | Lys | Ala | Met | Asn | |
|  | 435 |  |  |  |  | 440 |  |  |  |  | 445 |  |  |  |  | |
| cgg | aga | aag |  |  |  |  |  |  |  |  |  |  |  |  |  | 1353 |
| Arg | Arg | Lys | | | | | | | | | | | | | | |
|  | 450 |  | | | | | | | | | | | | | | |

<210> SEQ ID NO 3
<211> LENGTH: 502
<212> TYPE: PRT
<213> ORGANISM: Leucosporidium scottii

<400> SEQUENCE: 3

Met Ser Arg Thr Leu Pro Ile Ser Arg Leu Arg Gly Arg Ala Arg Pro
1               5                  10                  15

Ser Ser Ser Leu Leu Gln Leu Pro Thr Glu Leu Gln Lys Leu Ser Ser
            20                  25                  30

Ser Pro Thr Ser Ser Leu Arg His Ala Ser Pro Ser Arg Ser Ala Trp
        35                  40                  45

Thr Ser Ala Ile Pro Gly Leu Ser Ser Ala Thr Pro Phe Ala Ser Thr
    50                  55                  60

Ser Thr Ser Ser Leu Leu Ala Gly Ser Ser Lys Val Ala Leu Gln
65                  70                  75                  80

Asp Pro Leu Lys Pro Leu Gly Ala Glu Met Gly Leu Leu Arg Ser Asn
                85                  90                  95

Val Gln His Leu Leu Gly Ser Gly His Pro Ala Leu Asp Thr Ile Ala

-continued

```
            100                 105                 110
Lys Tyr Tyr Phe Gln Ala Glu Gly Lys His Val Arg Pro Met Leu Ile
        115                 120                 125
Leu Leu Met Ser Gln Ala Thr Asn Gly Leu Ala Pro Gly Trp Glu Gln
        130                 135                 140
Arg Arg Asp Gln Ala Ala Ala Glu Leu Lys Arg Glu Gln Gly Asp
145                 150                 155                 160
Glu Gly Leu Gly Gly Asp Asp Ile Asp Glu Pro Leu Ser Pro Pro Ser
                165                 170                 175
Val Leu Asn Asp Gln Asn Pro Ser Met Leu Ala Ser Ala Lys Ser Phe
                180                 185                 190
Phe Ser Asp Pro Leu Ala Ser Leu Arg Pro Ala Pro Thr Pro Thr Ser
            195                 200                 205
Ile Ala Gln Ser Ile His Gln Thr His Leu Leu Pro Ser Gln Arg Arg
        210                 215                 220
Leu Ala Glu Ile Thr Glu Met Ile His Val Ala Ser Leu Leu His Asp
225                 230                 235                 240
Asp Val Ile Asp Leu Ala Glu Thr Arg Arg Ser Ala Pro Ser Ala Pro
                245                 250                 255
Ser Leu Phe Gly Asn Lys Leu Ser Ile Leu Ala Gly Asp Phe Leu Leu
                260                 265                 270
Ala Arg Ala Ser Leu Ala Leu Ser Arg Leu Gly Ser Asn Glu Val Val
            275                 280                 285
Glu Leu Val Ala Ser Val Leu Ala Asn Leu Val Glu Gly Glu Val Met
        290                 295                 300
Gln Met Lys Gly Asn Val Pro Gly Lys Glu Gly Leu Leu Ala Gly Ala
305                 310                 315                 320
Gly Gly Gly Ser Thr Ala Lys Gly Pro Thr Pro Glu Ile Phe Asp His
                325                 330                 335
Tyr Met Lys Lys Thr Tyr Leu Lys Thr Ala Ser Leu Ile Ala Lys Ser
                340                 345                 350
Thr Arg Ala Thr Thr Ile Leu Gly Gly Cys Gly Val Lys Gln Gly Trp
            355                 360                 365
Ala Glu Gly Glu Lys Val Lys Asp Ile Ala Tyr Ser Tyr Gly Arg Asn
        370                 375                 380
Leu Gly Ile Ala Phe Gln Leu Val Asp Asp Met Leu Asp Phe Thr Ala
385                 390                 395                 400
Ser Ala Ala Gln Leu Gly Lys Pro Gly Gly Ala Asp Leu Lys Leu
                405                 410                 415

Gly Leu Ala Thr Ala Pro Ala Leu Tyr Ala Trp Glu Glu Phe Pro Glu
                420                 425                 430
Leu Gly Ala Met Ile Glu Arg Lys Phe Ala Gly Glu Asp Asp Val Glu
            435                 440                 445
Gln Ala Arg His Leu Ile Ser Arg Ser Ser Gly Ala Glu Arg Thr Ala
        450                 455                 460

Ala Leu Ala Ala Glu His Ser Lys Leu Ala Arg Gln Ala Leu Glu Gly
465                 470                 475                 480
Leu Pro Asp Ser Glu Ala Arg Thr Ala Leu Asp Asn Met Ala Arg Asp
                485                 490                 495
Thr Leu Ser Arg Lys Lys
                500
```

<210> SEQ ID NO 4
<211> LENGTH: 451
<212> TYPE: PRT
<213> ORGANISM: Aspergillus clavatus

<400> SEQUENCE: 4

Met Arg Ala Arg Thr Val Ser Ala Ser Gly Leu Ile Leu Ser Ser Arg
1               5                   10                  15

Thr Thr Thr Ser Thr Ser Ile Cys Trp Gln Cys Leu Arg Glu Asp Leu
            20                  25                  30

Leu Ser Asn Gln Val Gln Ile His Val Arg Lys Tyr His Pro Thr Arg
        35                  40                  45

Arg Lys Asp Val Ser Pro Phe Gly Ala Val Ser Ala Ala Gln Thr
    50                  55                  60

Ile Phe Lys Gly Leu Pro Lys Ala Pro Pro Gly Ile Ser Val Asp Pro
65                  70                  75                  80

Leu Arg Ile Val Gly Lys Glu Leu Lys Phe Leu Thr Lys Asn Ile Arg
                85                  90                  95

Gln Leu Leu Gly Ser Gly His Pro Thr Leu Asp Lys Val Ala Lys Tyr
            100                 105                 110

Tyr Thr Arg Ser Glu Gly Lys His Met Arg Pro Leu Leu Val Leu Leu
        115                 120                 125

Met Ser Gln Ala Thr Ala Leu Thr Pro Arg Gln Ser Arg Ser Asn Phe
    130                 135                 140

Thr Pro Ser Gln Met Val Asn Asp Pro Ile Ser Ser Pro Ser Val Leu
145                 150                 155                 160

Ala Asp Thr Asn Pro Asp Leu Ser Pro Leu Val Ser Lys Ser Ala Glu
                165                 170                 175

Ala Gln Tyr Asp Phe Ala Gly Asp Glu Asn Thr Leu Pro Thr Gln Arg
            180                 185                 190

Arg Leu Ala Glu Ile Thr Glu Leu Ile His Thr Ala Ser Leu Leu His
        195                 200                 205

Asp Asp Val Ile Asp Asn Ala Val Thr Arg Arg Ser Ser Asn Ser Ala
    210                 215                 220

Asn Leu Gln Phe Gly Asn Lys Met Ala Val Leu Ala Gly Asp Phe Leu
225                 230                 235                 240

Leu Gly Arg Ala Ser Val Ala Leu Ala Arg Leu Arg Asp Pro Glu Val
                245                 250                 255

Thr Glu Leu Leu Ala Thr Val Ile Ala Asn Leu Val Glu Gly Glu Phe
            260                 265                 270

Met Gln Leu Lys Asn Thr Ala Ala Asp Glu Lys Asn Pro Val Phe Thr
    275                 280                 285

Asp Gly Thr Ile Ser Tyr Tyr Leu Gln Lys Thr Tyr Leu Lys Thr Ala
290                 295                 300

Ser Leu Ile Ser Lys Ser Cys Arg Ala Ala Leu Leu Gly Ser
305                 310                 315                 320

Thr Pro Glu Val Val Asp Ala Ala Tyr Ala Tyr Gly Arg Asn Leu Gly
                325                 330                 335

Leu Ala Phe Gln Leu Val Asp Asp Leu Leu Asp Tyr Thr Val Ser Gly
            340                 345                 350

Val Glu Leu Gly Lys Pro Ala Gly Ala Asp Leu Glu Leu Gly Leu Ala
    355                 360                 365

Thr Ala Pro Leu Leu Phe Ala Trp Lys Gln Asn Pro Glu Leu Gly Pro
370                 375                 380

```
Leu Val Gly Arg Lys Phe Ser Arg Glu Gly Asp Val Gln Met Ala Arg
385                 390                 395                 400

Glu Leu Val Tyr Lys Ser Asp Gly Val Glu Gln Thr Arg Ala Leu Ala
            405                 410                 415

Gln Glu Tyr Ala Asp Lys Ala Ile Thr Ala Val Ser Asn Phe Pro Asp
            420                 425                 430

Ser Glu Ala Lys Ala Gly Leu Ile Gln Met Cys Glu Lys Ala Met Asn
        435                 440                 445

Arg Arg Lys
    450

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: primer
      DPS-1
<220> FEATURE:
<221> NAME/KEY: misc_feature
<222> LOCATION: (10)..(10)
<223> OTHER INFORMATION: n stands for any base
<220> FEATURE:
<221> NAME/KEY: misc_feature
<222> LOCATION: (13)..(13)
<223> OTHER INFORMATION: n stands for any base

<400> SEQUENCE: 5
aaggatcctn ytncaygayg aygt                                        24

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: primer
      DPS-1 1AS
<220> FEATURE:
<221> NAME/KEY: misc_feature
<222> LOCATION: (6)..(6)
<223> OTHER INFORMATION: n stands for any base
<220> FEATURE:
<221> NAME/KEY: misc_feature
<222> LOCATION: (15)..(15)
<223> OTHER INFORMATION: n stands for any base

<400> SEQUENCE: 6
arytgnadra aytcncc                                                17

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: primer L1S

<400> SEQUENCE: 7
gcagagacga ggcgatcggc c                                           21

<210> SEQ ID NO 8
<211> LENGTH: 15
<212> TYPE: DNA
<213> ORGANISM: Artificial Sequence
<220> FEATURE:
<223> OTHER INFORMATION: Description of Artificial Sequence: primer
      L7ASP
```

```
<400> SEQUENCE: 8
ggcctgctcg acatc                                                  15

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: primer L5S

<400> SEQUENCE: 9
tgggcagagg gagagaaggt c                                           21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: primer L4AS

<400> SEQUENCE: 10
gttggcgaga acggaagcga c                                           21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: primer L6S

<400> SEQUENCE: 11
gcaccagcac tctacgcgtg g                                           21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: primer L3AS

<400> SEQUENCE: 12
gttgccaaag agcgaaggag c                                           21

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: primer
      LN1-2

<400> SEQUENCE: 13
ttgcttctct cgcatatgtc gcggacactg ccg                              33

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence: primer LCH
```

```
<400> SEQUENCE: 14
acaagcttct acttcttcct cgacaatgt                                    29

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: primer A1S

<400> SEQUENCE: 15
gttactcgga ggtcgtctaa c                                            21

<210> SEQ ID NO 16
<211> LENGTH: 15
<212> TYPE: DNA
<213> ORGANISM: Artificial Sequence
<220> FEATURE:
<223> OTHER INFORMATION: Description of Artificial Sequence: primer
      A7ASP

<400> SEQUENCE: 16
caccagttca cgagc                                                   15

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: primer A5S

<400> SEQUENCE: 17
gttgtcgatg ctgcttatgc c                                            21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: primer A2AS

<400> SEQUENCE: 18
aatgacagtt gcaagcagtt c                                            21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: primer A6S

<400> SEQUENCE: 19
gcctggaagc agaaccctga g                                            21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: primer A3AS

<400> SEQUENCE: 20
caggacggcc atcttatttc c                                            21
```

```
<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence: primer AN2

<400> SEQUENCE: 21
aaggatccga tgagagctcg aacggtctcg gcc                           33

<210> SEQ ID NO 22
<211> LENGTH: 29
<212> TYPE: DNA
<213> ORGANISM: Artificial Sequence
<220> FEATURE:
<223> OTHER INFORMATION: Description of Artificial Sequence: primer ACH

<400> SEQUENCE: 22
acaagcttct actttctccg gttcatggc                               29
```